United States Patent
Majeed et al.

(10) Patent No.: US 11,052,125 B2
(45) Date of Patent: Jul. 6, 2021

(54) COMPOSITIONS FOR WEIGHT LOSS

(71) Applicants: Muhammed Majeed, Bangalore (IN); Kalyanam Nagabhushanam, East Windsor, NJ (US); Lakshmi Mundkur, Bangalore (IN); Sarang Bani, Bangalore (IN); Anjali Pandey, Bangalore (IN)

(72) Inventors: Muhammed Majeed, Bangalore (IN); Kalyanam Nagabhushanam, East Windsor, NJ (US); Lakshmi Mundkur, Bangalore (IN); Sarang Bani, Bangalore (IN); Anjali Pandey, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 11 days.

(21) Appl. No.: 16/396,902

(22) Filed: Apr. 29, 2019

(65) Prior Publication Data
US 2019/0328818 A1    Oct. 31, 2019

Related U.S. Application Data

(60) Provisional application No. 62/664,395, filed on Apr. 30, 2018.

(51) Int. Cl.
*A61K 36/8905* (2006.01)
*A61K 36/38* (2006.01)
*A61K 36/67* (2006.01)
*A61P 3/04* (2006.01)
*A61K 36/53* (2006.01)

(52) U.S. Cl.
CPC .......... *A61K 36/8905* (2013.01); *A61K 36/38* (2013.01); *A61K 36/53* (2013.01); *A61K 36/67* (2013.01); *A61P 3/04* (2018.01)

(58) Field of Classification Search
None
See application file for complete search history.

(56) References Cited

U.S. PATENT DOCUMENTS

| 5,804,596 A * | 9/1998 | Majeed | A61K 31/352 |
| | | | 514/455 |
| 2002/0187943 A1* | 12/2002 | Majeed | A61P 3/06 |
| | | | 514/27 |
| 2015/0238438 A1* | 8/2015 | Majeed | A61K 36/8905 |
| | | | 424/773 |

FOREIGN PATENT DOCUMENTS

JP    2001275614 A  * 10/2001

OTHER PUBLICATIONS

Kovesdy et al., Obesity and Kidney Disease: Hidden Consequences of the Epidemic, Can J Kidney Health Dis. 2017; 4:2054358117698669.

* cited by examiner

*Primary Examiner* — Terry A McKelvey
*Assistant Examiner* — Catheryne Chen

(57) ABSTRACT

The present invention discloses a composition comprising extracts of *Cyperus rotundus*, standardized to contain 3-5% w/w total stilbenes, extracts of *Garcinia* sp., standardized to contain 20% w/w garcinol and extracts of *Coleus forskohlii* standardized to contain not less than 10% w/w forskolin for the therapeutic management of diet induced obesity and weight gain and related conditions like liver dysfunction, NASH, NAFLD, liver cirrhosis, hypercholesterolemia, hyperlipidemia, kidney dysfunction by bringing about a reduction in body weight, increasing lean body mass and by normalizing the levels of liver enzymes, kidney markers and circulating lipids.

8 Claims, 2 Drawing Sheets

Normal control | High Fat Diet control | Total Stilbenes 50+ Garcinol 10 + Forskolin 25 + 10% Phospholipids + HFD | Total stilbenes 50+ Garcinol 10 + Forskolin 25 + HFD

COMPOSITIONS FOR WEIGHT LOSS

CROSS REFERENCE TO RELATED APPLICATION

This is a non-provisional filing claiming priority from U.S. provisional application No. U.S. 62/664,395 filed on 30 Apr. 2018.

BACKGROUND OF INVENTION

Field of Invention

The present invention relates to obesity management. Specifically the present invention relates to compositions containing extracts of *Cyperus rotundus, Garcinia* sp., *Coleus forskohlii* in effective ratios for managing obesity and related conditions in mammals.

DESCRIPTION OF PRIOR ART

Obesity is a condition in which there is excess build up of fat in the body. The national institutes of health has defined obesity as Body mass index (BMI) of 30 and above, a ratio of weight to height which correlate with the total body fat content (William Shiel, Medical Definition of Obesity, MedicineNet, https://www.medicinenet.com/script/main/art.asp?articlekey=11760 accessed 20 Apr. 2019). Obesity is a multi-factorial disorder which is caused due to both lifestyle and genetics, leading to the development of many diseases and disorders which include diabetes, hypertension, heart diseases, stroke, neurodegenerative diseases, cancer, sleep apnea, arthritis and many more.

Obesity also leads to the development of liver dysfunction by being the most common cause for non-alcoholic fatty liver disease (NAFLD) and non-alcoholic steato hepatitis (NASH) (Sarwar et al., Obesity and nonalcoholic fatty liver disease: current perspectives, Diabetes Metab Syndr Obes. 2018; 11: 533-542). The levels of circulating lipids are elevated in people with obesity (Klop et al., Dyslipidemia in Obesity: Mechanisms and Potential Targets, Nutrients. 2013 April; 5(4): 1218-1240). Further, kidney functions are also disrupted (Kovesdy et. al., Obesity and Kidney Disease, Hidden Consequences of the Epidemic, Can J Kidney Health Dis. 2017; 4: 2054358117698669) in obese individuals thereby augmenting the overall disruption and deterioration in health and well being.

There are many treatment methods being employed for the management of obesity which include diet restrictions and increase in physical activity. Drugs like orlistat are associated with side effects, induce limited weight reduction and are being withdrawn from the market due to low risk vs. benefit ratio. Natural molecules from different plant sources offer a safe and efficacious option for weight management and are now finding their way in managing obesity and related conditions.

The use of natural molecules for obesity management is well described in the scientific art.

Extracts of *Garcinia cambogia*, have been reported to have a weight loss potential. U.S. Pat. No. 7,063,861, discloses a weight loss composition containing garcinol and hydroxycitric acid (HCA) and optionally with anthocyanins. U.S. Pat. No. 8,329,743 also discloses a weight loss formulation containing garcinol, pterostilbene and anthocyanin. U.S. patent application Ser. No. 16/007,212 discloses the anti obesity potential of garcinol per se. Extracts of other plant materials like *Cyperus rotundus* (U.S. Pat. Nos. 9,387,193, 9,782,450) and *Coleus forskohlii* (EP0977564) are also used for reducing body weight and managing obesity and related conditions.

Combination drug therapies are also used for treating obesity (Gadde and Allision, Combination Pharmaceutical Therapies for Obesity, Expert Opin Pharmacother. 2009 April; 10(6): 921-925). Combinations of natural molecules can synergistically increase the efficacy of the treatment. The present invention discloses one such combination comprising extracts of *Cyperus rotundus*, standardized to contain 3-5% total stilbenes, extracts of *Garcinia* sp., standardized to contain 20% garcinol and extracts of *Coleus forskohlii* standardized to contain not less than 10% forskolin for the therapeutic management of obesity and related conditions.

The three natural extracts used in the combination reduce obesity by different mechanisms, Forskolin the cAMP activator, is known to activate hormone sensitive lipase and induce fat hydrolysis and increase mitochondrial uncoupling protein to tranactivate brown adipocytes. Garcinol is reported to modify the gut microbiome in favor of *Akkermansia* species apart from activating the genes related to adipocyte browning, while 3-5% total stilbenes from cyperus prevent adipogenesis, increase adiponectin and reduce cholesterol and leptin leading to an overall loss in weight.

It is the principle object of the invention to disclose a composition comprising extracts of *Cyperus rotundus*, standardized to contain 3-5% total stilbenes, extracts of *Garcinia* sp., standardized to contain 20% garcinol and extracts of *Coleus forskohlii* standardized to contain not less than 10% forskolin for the therapeutic management of obesity.

It is another object of the invention to disclose a method for the therapeutic management of obesity related conditions using a composition comprising extracts of *Cyperus rotundus*, standardized to contain 3-5% total stilbenes, extracts of *Garcinia* sp., standardized to contain 20% garcinol and extracts of *Coleus forskohlii* standardized to contain not less than 10% forskolin.

The present invention solves the above mentioned objectives and provides further related advantages.

SUMMARY OF THE INVENTION

The present invention discloses a composition comprising extracts of *Cyperus rotundus*, standardized to contain 3-5% w/w total stilbenes, extracts of *Garcinia* sp., standardized to contain 20% w/w garcinol and extracts of *Coleus forskohlii* standardized to contain not less than 10% w/w forskolin for the therapeutic management of diet induced obesity and weight gain by bringing about a reduction in body weight and increasing lean body mass.

The invention also discloses the use of the composition comprising extracts of *Cyperus rotundus*, standardized to contain 3-5% w/w total stilbenes, extracts of *Garcinia* sp., standardized to contain 20% w/w garcinol and extracts of *Coleus forskohlii* standardized to contain not less than 10% w/w forskolin, in managing obesity related conditions selected from the group comprising liver dysfunction, NASH, NAFLD, liver cirrhosis, hypercholesterolemia, hyperlipidemia, kidney dysfunction by normalizing the levels of liver enzymes, kidney markers and circulating lipids.

Other features and advantages of the present invention will become apparent from the following more detailed description, taken in conjunction with the accompanying images, which illustrate, by way of example, the principle of the invention.

DESCRIPTION OF PREFERRED EMBODIMENTS

Figure 1:
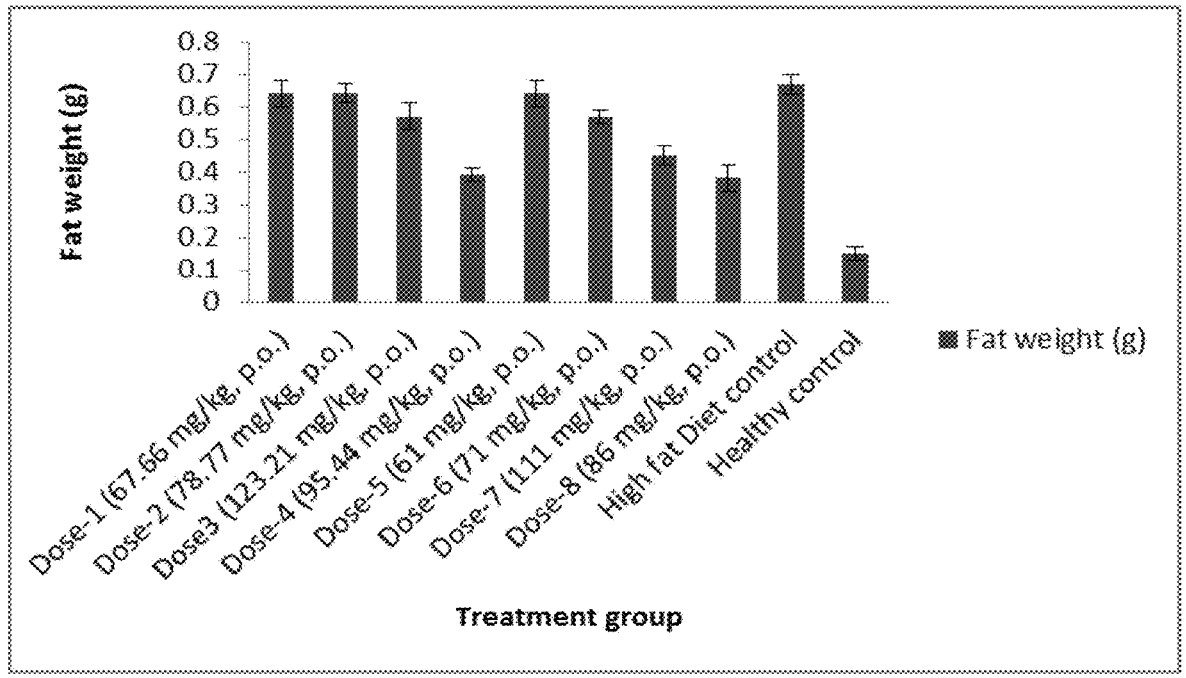
FIG. 1 is graphical representation showing the fat pad weight of C57BL/6J mice treated with different formulations.

In a most preferred embodiment, the present invention discloses a method for preventing diet induced weight gain and related conditions in mammals, said method comprising step of administering a composition comprising extracts of Cyperus rotundus, standardized to contain 3-5% w/w total stilbenes, extracts of Garcinia sp., standardized to contain 20% w/w garcinol and extracts of Coleus forskohlii standardized to contain not less than 10% w/w forskolin in effective doses to said mammals to bring about a reduction in body weight and increasing lean body mass. In a related aspect, the effective doses of the total stilbenes, forskolin and garcinol are 50 mg/day, 25 mg/day and 10 mg/day respectively. In a related aspect, the composition further comprises of Piper nigrum extract standardized to contain not less than 10% w/w piperine in an effective dose of 1 mg/day. In another related aspect, the composition further comprises of 10% w/w phospholipids. In another related aspect, the stilbenes of Cyperus rotundus extracts consists of picetannol, scirpusin A and scirpusin B. In another related aspect, the Garnicia sp. Include Garcinia cambogia and Garcinia indica. In another related aspect, the related conditions of diet induced weight gain are selected from the group comprising, but not limited to, liver dysfunction, NASH, NAFLD, liver cirrhosis, hypercholesterolemia, hyperlipidemia, kidney dysfunction. In another related aspect, the composition prevents diet induced hypercholesterolemia and hyperlipidemia by decreasing the levels of total cholesterol, triglycerides, VLDL and LDL and increasing the levels of HDL. In yet another related aspect, the composition prevents diet induced liver dysfunction, NASH, NAFLD, cirrhosis and improves liver function by normalizing the elevated liver enzymes selected from the group consisting of SGOT and SGPT. In another related aspect, the composition prevents diet induced kidney damage and improves kidney function by normalizing elevated circulating levels of creatinine, uric acid, blood urea nitrogen, and total protein. In yet another related aspect the mammals is human.

In a related embodiment the composition is formulation with pharmaceutically/nutraceutically accepted excipients, preservatives, antioxidants, and adjuvants and administered orally in the form of pharmaceutically/nutraceutically acceptable excipients, adjuvants, diluents or carriers and administered in the form of tablets, capsules, syrups, gummies, chewing gum, powders, suspensions, emulsions, chewables, candies, lozenges or eatables.

In another related embodiment, the invention discloses a composition comprising extracts of Cyperus rotundus, standardized to contain 3-5% w/w total stilbenes, extracts of Garcinia sp., standardized to contain 20% w/w garcinol and extracts of Coleus forskohlii standardized to contain not less than 10% w/w forskolin for use in preventing diet induced and related conditions. In a related aspect, the composition is administered in effective doses of 50 mg/day total stilbenes, 25 mg/day forskolin and 10 mg/day garcinol. In a related aspect, the composition further comprises of Piper nigrum extract standardized to contain not less than 10% w/w piperine in an effective dose of 1 mg/day. In another related aspect, the composition further comprises of 10% w/w phospholipids. In another related aspect, the stilbenes of Cyperus rotundus extracts consists of picetannol, scirpusin A and scirpusin B. In another related aspect, the Garnicia sp. include Garcinia cambogia and Garcinia indica. In another related aspect, the related conditions of diet induced weight gain are selected from the group comprising, but not limited to, liver dysfunction, NASH, NAFLD, liver cirrhosis, hypercholesterolemia, hyperlipidemia, kidney dysfunction. In another related aspect, the composition prevents diet induced hypercholesterolemia and hyperlipidemia by decreasing the levels of total cholesterol, triglycerides, VLDL and LDL and increasing the levels of HDL. In yet another related aspect, the composition prevents diet induced liver dysfunction, NASH, NAFLD, cirrhosis and improves liver function by normalizing the elevated liver enzymes selected from the group consisting of SGOT and SGPT. In another related aspect, the composition prevent diet induced kidney damage and improves kidney function by normalizing elevated circulating levels of creatinine, uric acid, blood urea nitrogen, and total protein. In yet another related aspect the mammals is human.

In a related embodiment the composition is formulation with pharmaceutically/nutraceutically accepted excipients, preservatives, antioxidants, and adjuvants and administered orally in the form of pharmaceutically/nutraceutically acceptable excipients, adjuvants, diluents or carriers and administered in the form of tablets, capsules, syrups, gummies, chewing gum, powders, suspensions, emulsions, chewables, candies, lozenges or eatables.

The following illustrative examples further describe in detail the preferred embodiments of the invention:

EXAMPLES

Example 1: Treatment

Male C57BL/6J mice at 5 weeks of age were used in the invention. After 1 week of acclimation, animals were randomly distributed into four groups of 8 animals each as described in the following Table 1: The control group animals were fed with normal diet and the research control with high fat diet (HFD) along with formulation as in Table 1

TABLE 1

Treatment group (Cyperus ext., Garcinol and Forskolin Phospolipids and piperine composition) dose ratio/measurement

| | Cyperus ext. (5% stilbenes) mg/day | 20% Forskolin mg/day | 20% Garcinol mg/day | Piperine mg/day | Phospholipids |
|---|---|---|---|---|---|
| HFD + Dose I | 50 | — | 10 | 1 | 10% |
| HFD + Dose-II | 50 | — | 20 | 1 | 10% |
| HFD + Dose-III | 50 | 50 | 10 | 1 | 10% |

TABLE 1-continued

Treatment group (Cyperus ext., Garcinol and Forskolin Phospholipids and piperine composition) dose ratio/measurement

| | Cyperus ext. (5% stilbenes) mg/day | 20% Forskolin mg/day | 20% Garcinol mg/day | Piperine mg/day | Phospholipids |
|---|---|---|---|---|---|
| HFD + Dose-IV | 50 | 25 | 10 | 1 | 10% |
| HFD + Dose-V | 50 | — | 10 | 1 | — |
| HFD + Dose-VI | 50 | — | 20 | 1 | — |
| HFD + Dose-VII | 50 | 50 | 10 | 1 | — |
| HFD + Dose-VIII | 50 | 25 | 10 | 1 | — |
| HFD Control | — | — | — | — | — |

The diet intake of animals was monitored every day and the body weight was recorded. All animal experimental protocol used in this study was approved by Institutional Animal Care and Use Committee of the National Kaohsiung Marine University (IACUC, NKMU). At the end of the study, all animals were fasted overnight and sacrificed by $CO_2$ asphyxiation. Blood samples were collected from the heart for biochemical analysis. Liver, spleen, kidney and fat pads (perigonadal, retroperitoneal and mesenteric fat) were immediately removed. Body weight was monitored and the average body weight of each group was expressed as the mean±SE. Statistical analysis was done by Student's t test and compared with HFD group.

Example 2: Body Weight Measurement

The animals were weighed after one month (Table 2) and the animals fed with HFD showed increased body weight. The composition at the dose of Cyp 50+ For 25+Gar 10, with and without phospholipids significantly reduced increase in body weight even when administered with high fat diet.

TABLE 2

Formulation/composition (Cyperus ext. (total stilbenes), Garcinol and Forskolin Phospolipids and piperine composition)

| Formulation | Body weight After 1 month |
|---|---|
| With 10% Phospholipids | |
| Cyp 50 + Gar 10 | 26.03 ± 0.82 |
| Cyp 50 + Gar 20 | 28.60 ± 0.59 |
| Cyp 50 + For 50 + Gar 10 | 27.35 ± 1.09 |
| Cyp 50 + For 25 + Gar 10 | 24.20 ± 1.08 |
| Without Phospholipids | |
| Cyp 50 + Gar 10 | 28.92 ± 0.98 |
| Cyp 50 + Gar 20 | 27.99 ± 1.05 |
| Cyp 50 + For 50 + Gar 10 | 26.13 ± 1.00 |
| Cyp 50 + For 25 + Gar 10 | 24.79 ± 1.25 |
| HFD | 29.08 ± 0.65 |
| Control | 22.50 ± 1.33 |

The body weight of the animals were also measured after 90 days before sacrifice.

Table 3 shows the body weight of the animals after the 90 day period.

TABLE 3

Body weight Measurement (gm)

| Treatment group | Day 90 |
|---|---|
| Healthy control | 26.27 ± 1.53** |
| HFD Diet control | 32.76 ± 0.60 |
| Cyperus ext 50 + Garcinol 10 + 10% Phospholipids | 27.46 ± 0.99* |
| Cyperus ext 50 + Garcinol 20 + 10% Phospholipids | 27.36 ± 0.59* |
| Cyperus ext 50 + Garcinol 10 + Forskolin 50 + 10% Phospholipids | 27.69 ± 0.74* |
| Cyperus ext 50 + Garcinol 10 + Forskolin 25 + 10% Phospholipids | 23.90 ± 1.26** |
| Cyperus ext 50 + Garcinol 10 | 26.62 ± 1.07* |
| Cyperus ext 50 + Garcinol 20 | 26.27 ± 1.44* |
| Cyperus ext 50 + Garcinol 10 + Forskolin 50 | 26.67 ± 1.44* |
| Cyperus ext 50 + Garcinol 10 + Forskolin 25 | 22.14 ± 1.20** |

**$P < 0.01$ and
*$P < 0.05$

High fat diet significantly increased the body weight of the animals compared to the normal control. The composition comprising Cyperus ext 50+ Garcinol 10+Forskolin 25 (Dose 8) significantly inhibited the increase in body weight compared to all the other dosages by 32.41%. The same dosage actives along with phospholipids (Dose 4) was also effective in inhibiting the body weight by 27% (Table 4)

TABLE 4

Percentage Body weight Inhibition by the formulation

| Treatment group | % Inhibition |
|---|---|
| Healthy control | — |
| HFD Diet control | — |
| Cyperus ext. 50 + Garcinol 10 + 10% Phospholipids | 16.17% |
| Cyperus ext. 50 + Garcinol 20 + 10% Phospholipids | 16.48% |
| Cyperus ext. 50 + Garcinol 10 + Forskolin 50 + 10% Phospholipids | 15.47% |
| Cyperus ext. 50 + Garcinol 10 + Forskolin 25 + 10% Phospholipids | 27.04% |
| Cyperus ext. 50 + Garcinol 10 | 18.74 |
| Cyperus ext. 50 + Garcinol 20 | 19.81% |
| Cyperus ext. 50 + Garcinol 10 + Forskolin 50 | 18.58% |
| Cyperus ext. 50 + Garcinol 10 + Forskolin 25 | 32.41% |

Figure 2:
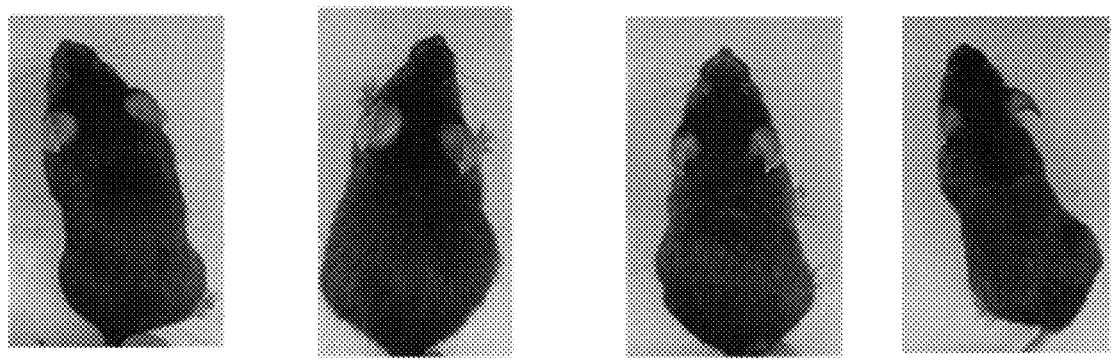
FIG. 2 shows the decrease in body weight of test animals using a composition comprising total stilbenes, garcinol and forskolin at the dosages of 50 mg/day, 10 mg/day and 25 mg/day respectively.

The fat pad weight was also less in the treatment group administered with Cyperus extract, garcinol and forskolin at the dosages of 50 mg/day, 10 mg/day and 25 mg/day respectively (dose 8), (FIG. 1) indicating that the formulation prevents diet induced weight gain and promotes lean body mass by preventing fat accumulation. The animals also visually showed decreased weight gain after the 90 day treatment period even when administered with high fat diet (FIG. 2).

Example 3: Changes in Lipid Profile

The circulating levels of lipids, viz total cholesterol, triglycerides, LDL, VLDL and HDL, was evaluated after the 90 day treatment using standard protocol.

Figure 3:
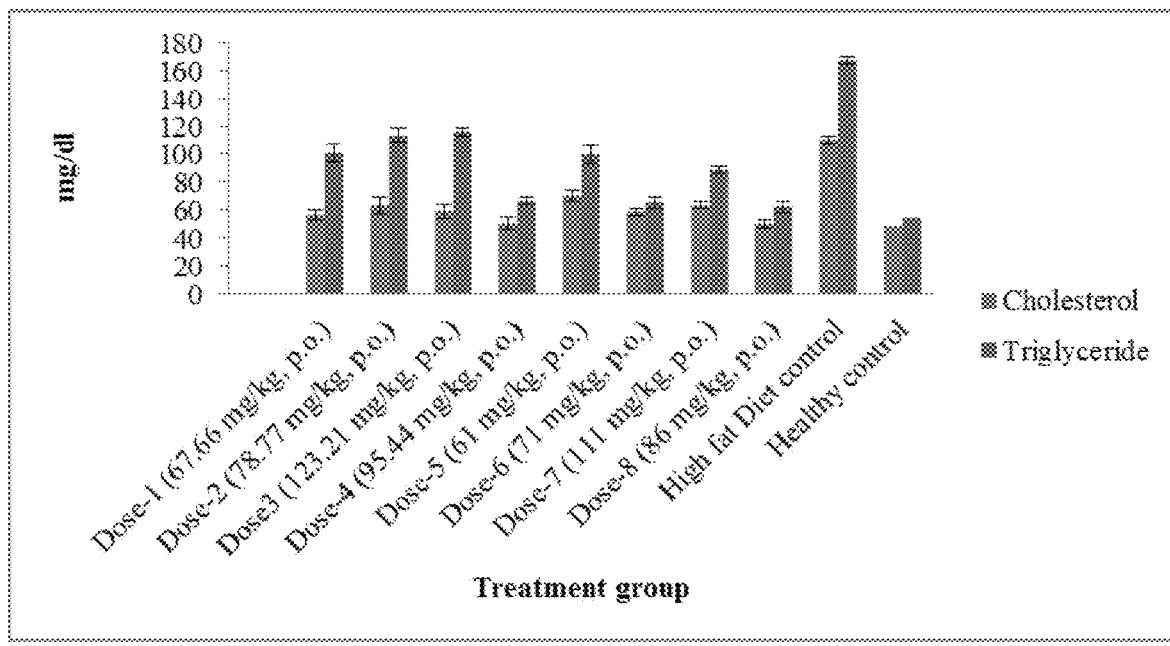
FIG. 3 is graphical representation showing the levels of total cholesterol and triglycerides in C57BL/6J mice treated with different formulations.

High fat diet significantly increased the cholesterol, triglycerides levels and the formulation comprising Cyperus extract, garcinol and forskolin at the dosages of 50 mg/day, 10 mg/day and 25 mg/day respectively (dose 8), was very effective in preventing increase in cholesterol and triglyceride levels (FIG. 3), compared to the other dosages. The formulation comprising Cyperus extract, garcinol and forskolin at the dosages of 50 mg/day, 10 mg/day and 25 mg/day respectively (dose 8) also significantly decreased the circulating levels of LDL and VLDL and increased the levels of HDL (Table 5) compared to other dosages.

The formulation thus plays an effective role in preventing hypercholesterolemia, and hyperlipidemia induced by high fat diet.

TABLE 5

Levels of VLDL, LDL and HDL in treatment groups after 90 days

| Groups | VLDL (mg/dl) | LDL (mg/dl) | HDL (mg/dl) |
|---|---|---|---|
| Normal control | 10.9 ± 0.50** | 7.52 ± 0.32** | 30.33 ± 2.18** |
| High fat Diet control | 33.64 ± 0.89 | 50.52 ± 1.45 | 16.67 ± 0.33 |
| Cyperus ext. 50 + Garcinol 10 + 10% Phospholipids + HFD | 20.15 ± 1.02** | 12.83 ± 0.42** | 23.67 ± 0.66** |
| Cyperus ext. 50 + Garcinol 20 + 10% Phospholipids + HFD | 22.85 ± 1.45** | 18.07 ± 0.34** | 22.33 ± 0.76* |
| Cyperus ext. 50 + Garcinol 10 + Forskolin 50 + 10% Phospholipids + HFD | 23.3 ± 0.94** | 12.44 ± 0.23** | 23.67 ± 1.16** |
| Cyperus ext. 50 + Garcinol 10 + Forskolin 25 + 10% Phospholipids + HFD | 13.3 ± 0.57** | 13.40 ± 0.34** | 23.80 ± 1.20** |
| Cyperus ext. 50 + Garcinol 10 + HFD | 19.9 ± 0.5** | 27.02 ± 0.23* | 23.33 ± 0.33** |
| Cyperus ext. 50 + Garcinol 20 + HFD | 13.05 ± 1.26** | 21.70 ± 0.44* | 24.00 ± 1.15** |
| Cyperus ext. 50 + Garcinol 10 + Forskolin 50 + HFD | 14.75 ± 0.89** | 20.02 ± 0.54* | 25.33 ± 0.88** |
| Cyperus ext. 50 + Garcinol 10 + Forskolin 25 + HFD | 12.45 ± 0.49** | 12.42 ± 0.33** | 26.67 ± 0.66** |

**$P < 0.01$ and
*$P < 0.05$

Example 4: Improvement in Liver Function

It is well known in the scientific literature that high fat diet causes liver dysfunction leading to the development of many conditions like NAFLD, NASH, cirrhosis etc. The effect of different formulations on liver function was assessed by measuring the liver markers SGOT and SGPT.

Figure 4:
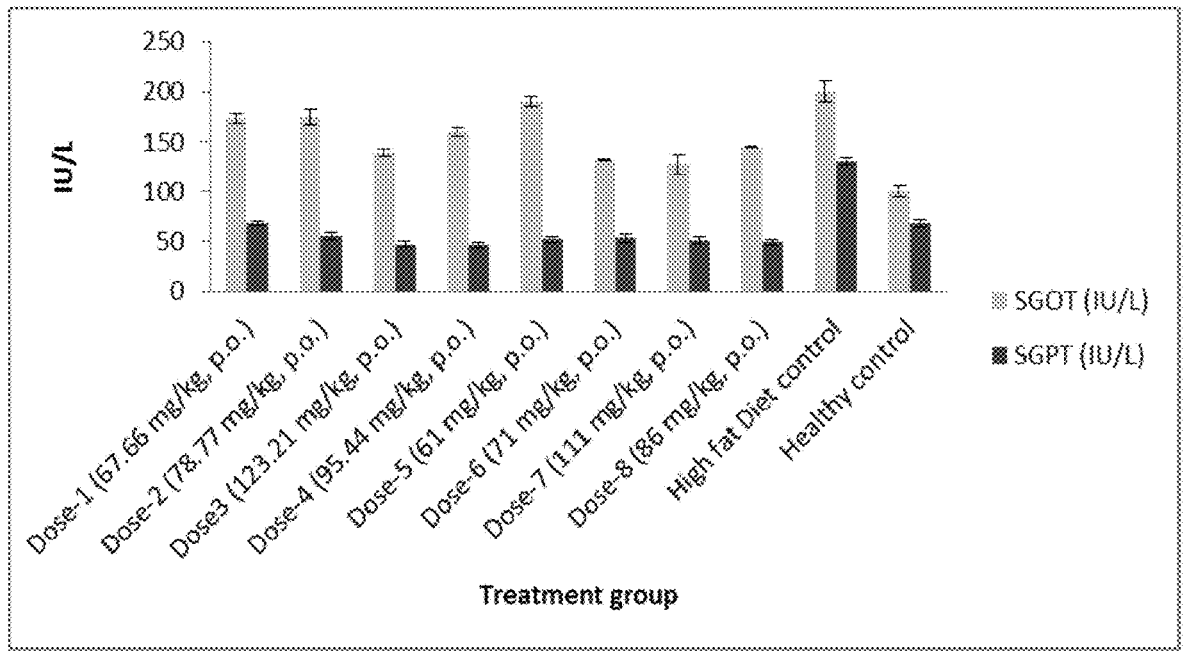
FIG. 4 is graphical representation showing the levels of liver enzymes in C57BL/6J mice treated with different formulations.

The results indicated that high fat diet significantly increased the levels of liver markers SGOT and SGPT indicating increased liver damage and dysfunction. The formulation comprising Cyperus extract, garcinol and forskolin at the dosages of 50 mg/day, 10 mg/day and 25 mg/day respectively (dose 8), was effective in preventing high fat diet induced liver damage and dysfunction which is evident by the decreased levels of the liver enzymes (FIG. 4).

Example 5: Effect of Different Formulation on Kidney Function

High fat diet, increased weight gain and obesity has a serious effect on kidney function. The effect of different formulations on kidney function was assessed by measuring the kidney markers creatinine, uric acid, blood urea nitrogen (BUN) and total protein.

The results indicated that high fat diet significantly damaged the kidneys as evident with the increase in levels of kidney markers. The formulation comprising Cyperus extract, garcinol and forskolin at the dosages of 50 mg/day, 10 mg/day and 25 mg/day respectively (dose 8), was effective in preventing high fat diet induced kidney damage and dysfunction by normalizing the levels of the kidney markers (Table 6).

TABLE 6

Effect of different formulations on kidney function

| Groups | Creatinine (mg/dl) | Uric acid (mg/dl) | BUN (mg/dl) | Total Protein (g/dl) |
|---|---|---|---|---|
| Normal control | 0.50 ± 0.03* | 3.36 ± 0.47* | 161.33 ± 4.31** | 4.93 ± 0.23* |
| High fat Diet control | 0.94 ± 0.23 | 5.98 ± 0.08 | 238.33 ± 4.06 | 6.67 ± 0.33 |
| Cyperus ext. 50 + Garcinol 10 + 10% Phospholipids + HFD | 0.76 ± 0.03 | 4.61 ± 0.68 | 70.00 ± 3.51** | 5.53 ± 0.12 |
| Cyperus ext. 50 + Garcinol 20 + 10% Phospholipids + HFD | 0.78 ± 0.06 | 5.10 ± 0.47 | 67.33 ± 2.33** | 5.17 ± 0.26* |
| Cyperus ext. 50 + Garcinol 10 + Forskolin 50 + 10% Phospholipids + HFD | 0.73 ± 0.03 | 4.16 ± 0.37* | 58.00 ± 3.50** | 4.47 ± 0.61** |
| Cyperus ext. 50 + Garcinol 10 + Forskolin 25 + 10% Phospholipids + HFD | 0.80 ± 0.05 | 3.82 ± 0.58* | 71.00 ± 2.52** | 4.80 ± 0.25** |
| Cyperus ext. 50 + Garcinol 10 + HFD | 0.87 ± 0.03 | 4.14 ± 0.21* | 52.00 ± 3.42** | 5.73 ± 0.26 |
| Cyperus ext. 50 + Garcinol 20 + HFD | 0.83 ± 0.06 | 4.29 ± 0.14 | 66.67 ± 3.38** | 4.97 ± 0.39* |
| Cyperus ext. 50 + Garcinol 10 + Forskolin 50 + HFD | 0.77 ± 0.08 | 5.26 ± 0.36 | 54.67 ± 1.76** | 5.53 ± 0.33 |
| Cyperus ext. 50 + Garcinol 10 + Forskolin 25 + HFD | 0.72 ± 0.10 | 4.18 ± 0.30* | 80.00 ± 4.53** | 4.33 ± 0.22** |

**$P < 0.01$ and
*$P < 0.05$

Thus, the formulation comprising *Cyperus* extract, garcinol and forskolin at the dosages of 50 mg/day, 10 mg/day and 25 mg/day respectively synergistically reduce diet induced weight gain and can be use as an effective supplement for the management of obesity and related conditions. The formulation in along with 10% phospholipids was also effective in reducing weight induced by high fat diet.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method for therapeutic management of kidney dysfunction in mammals in need thereof, said method comprising step of administering a composition consisting essentially of extracts of *Cyperus rotundus*, standardized to contain 3-5% w/w total stilbenes, extracts of *Garcinia* sp., standardized to contain 20% w/w garcinol, extracts of *Coleus forskohlii* standardized to contain not less than 10% w/w forskolin and 10% phospholipids in effective doses to said mammals to bring about a reduction in the elevated levels of markers of kidney damage.

2. The method as in claim 1, wherein the effective doses of the total stilbenes, forskolin and garcinol are 50 mg/day, 25 mg/day and 10 mg/day respectively.

3. The method as in claim 1, wherein the stilbenes of *Cyperus rotundus* extracts consists of picetannol, scirpusin A and scirpusin B.

4. The method as in claim 1, wherein the *Garnicia* sp. include *Garcinia cambogia* and *Garcinia indica*.

5. The method as in claim 1, wherein the kidney dysfunction is induced by high fat diet.

6. The method as in claim 1, wherein the markers of kidney dysfunction is selected from the group consisting of creatinine, uric acid, blood urea nitrogen, and total protein.

7. The method as in claim 1, wherein the mammal is human.

8. The method as in claim 1, wherein the composition is formulated with pharmaceutically/nutraceutically accepted excipients, preservatives, bioavailability enhancers, antioxidants, and adjuvants and administered orally in the form of tablets, capsules, syrups, gummies, chewing gum, powders, suspensions, emulsions, chewables, candies, lozenges or eatables.

* * * * *